(12) United States Patent
Ishitsubo (10) Patent No.: US 8,367,107 B2
(45) Date of Patent: Feb. 5, 2013

(54) SOLID PHARMACEUTICAL PREPARATION

(75) Inventor: Naoki Ishitsubo, Ono (JP)

(73) Assignee: Nippon Zoki Pharmaceutical Co., Ltd., Osaka-shi (JP)

( * ) Notice: Subject to any disclaimer, the term of this patent is extended or adjusted under 35 U.S.C. 154(b) by 752 days.

(21) Appl. No.: 12/225,498

(22) PCT Filed: Mar. 30, 2007

(86) PCT No.: PCT/JP2007/057221
§ 371 (c)(1),
(2), (4) Date: Sep. 23, 2008

(87) PCT Pub. No.: WO2007/114376
PCT Pub. Date: Oct. 11, 2007

(65) Prior Publication Data
US 2009/0280174 A1    Nov. 12, 2009

(30) Foreign Application Priority Data

Mar. 30, 2006  (JP) ................................. 2006-093207

(51) Int. Cl.
*A61K 9/24* (2006.01)
(52) U.S. Cl. .......................... 424/472; 424/464; 424/468
(58) Field of Classification Search ........... 424/464–489
See application file for complete search history.

(56) References Cited

U.S. PATENT DOCUMENTS

| | | | |
|---|---|---|---|
| 5,395,626 A | 3/1995 | Kotwal et al. | |
| 6,159,501 A * | 12/2000 | Skinhoj | 424/461 |
| 6,221,394 B1 * | 4/2001 | Gilbert et al. | 424/473 |
| 6,780,891 B2 * | 8/2004 | Senanayake et al. | 514/646 |
| 2002/0165248 A1 | 11/2002 | Wimmer et al. | |
| 2003/0068375 A1 * | 4/2003 | Wright et al. | 424/468 |
| 2003/0180352 A1 | 9/2003 | Patel et al. | |
| 2004/0076669 A1 * | 4/2004 | Bartholomaus et al. | 424/468 |
| 2005/0089570 A1 * | 4/2005 | Cruz et al. | 424/468 |
| 2006/0018962 A1 | 1/2006 | Eivaskhani et al. | |

FOREIGN PATENT DOCUMENTS

| | | |
|---|---|---|
| CA | 2229621 A1 | 9/1998 |
| EP | 0 754 465 A1 | 1/1997 |
| EP | 0 864 325 A2 | 9/1998 |
| JP | A-08-020537 | 1/1996 |
| JP | A-08-169813 | 7/1996 |
| JP | A-09-510709 | 10/1997 |
| JP | A-10-251149 | 9/1998 |
| JP | A-2000-351732 | 12/2000 |
| JP | A-2002-527384 | 8/2002 |
| JP | A-2004-288138 | 10/2004 |
| JP | A-2005-537221 | 12/2005 |
| WO | WO 95/26753 A1 | 10/1995 |
| WO | WO 02/087549 A1 | 11/2002 |
| WO | WO 2004/078173 A1 | 9/2004 |

OTHER PUBLICATIONS

Dr. Li Ii, Shanghai Colorcon Coating Technology Limited, "High Performance of Partially Pregelatinized Starch as a New Pharmaceutical Excipient in the Preparation of Tablets," 1994, China Academic Journal Electronic Publishing House, pp. 23-25 (with English-language Translation).
Aug. 30, 2010 Chinese Office Action issued in Application No. 200780011267.9.
Oct. 27, 2011 Office Action issued in U.S. Appl. No. 11/663,421.
Charlet et al. "Chiroptical Filters from Aqueous (Hydroxypropyl) cellulose Liquid Crystals" Journal of Applied Polymer Science 1989, 37, 2517-2527.
Friderichs et al. "Opioids with Clinical Relevance" in Analgesics: From Chemistry and Pharmacology to Clinical Application Buschman et al. Eds. Wiley-VCH 2002, p. 228-229.
Symecko et al. In The Effect of Compaction Force and Type of Pregelatinized Starch on the Dissolution of Acetaminophen; Drug Development and Industrial Pharmacy 1997, 23, and 229-238.
Edited by Japan Pharmaceutical Excipients Council, Iyakushin Tenkabustu Jiten, 1$^{st}$ Edition Jan. 14, 1993.
Office Action in U.S. Appl. No. 11/663,421; mailed; May 13, 2009.
Office Action in U.S. Appl. No. 11/663,421; mailed Jan. 26, 2010.
International Search Report of Application No. PCT/JP2005/008935; mailed May 4, 2006 (with translation).

* cited by examiner

Primary Examiner — Michael G Hartley
Assistant Examiner — Micah-Paul Young
(74) Attorney, Agent, or Firm — Oliff & Berridge, PLC (57) ABSTRACT

It is intended to provide a long-acting solid pharmaceutical preparation which has an immediate release part and a sustained release part containing tramadol or a pharmaceutically acceptable salt thereof, is fast-acting and stably has an excellent release property showing little pH dependency in the initial elution. The invention relates to a long-acting solid pharmaceutical preparation characterized by having an immediate release part and a sustained release part, containing tramadol or a pharmaceutically acceptable salt thereof as an active ingredient in both parts and containing partially pregelatinized starch and an excipient as additives in the immediate release part. The preparation of the invention is a long-acting preparation in which an effective blood concentration is reached rapidly after taking it for rapid pain-relief and a drug action can be sustained for a long time thereafter and is practical as a preparation showing a stable, pH-independent and rapid initial elution behavior and, further, having a sufficient hardness enough to meet the need for avoidance of defacement, cracking, chipping, etc. during tablet coating.

10 Claims, 5 Drawing Sheets

SOLID PHARMACEUTICAL PREPARATION

TECHNICAL FIELD

The present invention relates to a solid pharmaceutical preparation which has an immediate release part and a sustained release part containing tramadol as an active ingredient.

BACKGROUND ART

Technique for producing a sustained release drug has been developed for various types of drugs to improve patients' compliance along with the advancement of manufacturing techniques. A sustained release drug has many benefits in efficacy and safety such as effectively induced pharmaceutical potency with a reduced number of administrations as well as a decreased incidence of side effect or toxicity owing to lasting drug efficacy compared with a typical immediate release drug.

However, drugs, such as an analgesic, which are also needed to take effect immediately, are also required to take effect immediately after an effective blood concentration is reached rapidly after taking it for rapid pain-relief, or the like. A bilayer tablet including an immediate release part and a sustained release part, a long-acting preparation combining immediate release granules and sustained release granules, and the like have been developed as a preparation that has both fast-acting and long-acting properties.

The long-acting preparation is considered as more excellent preparation when it is more hardly subjected to effect of physiological factors or the like of food and digestive tract and also has smaller intraindividual and/or interindividual variation in order that the blood concentration of a drug is maintained at an appropriate level for an appropriate period of time. To obtain a stable blood concentration, an oral preparation needs to be prepared to have physiological properties in digestive tract, especially not to be subject to pH. A multilayer tablet including an immediate release part and a sustained release part, for example, provides delayed initial elution depending on a tablet making method and/or great variation in the release of a medicinal ingredient depending on pH of eluate. Such phenomena may occur during production using a continuous tableting machine for massproduction, due probably to mixing of a sustained release component into an immediate release part caused by attaching or remaining of a sustained release part within the machine.

A long-acting preparation has been studied to reach an effective blood concentration rapidly after administration and sustain its efficacy for a long period of time for an active analgesic ingredient such as tramadol which is an active ingredient of a solid pharmaceutical preparation of the present invention. A multilayer preparation with a form containing an immediate release phase and a sustained release phase that contains at least one kind of opioid analgesic agent has been disclosed (see Patent Document 1). However, there is no description in Patent Document 1 about either a long-acting preparation that has an excellent release property showing little pH dependency in the initial elution of opioid or a technique for making such preparation.
[Patent Document 1]
Japanese Patent Application Publication No. JP-A-10-251149

DISCLOSURE OF THE INVENTION

Problem to be Solved by the Invention

It is an object of the present invention to provide a long-acting solid pharmaceutical preparation containing tramadol as an active ingredient, having an excellent fast-acting release property stably with little pH dependency in the initial elution, and having a sufficient hardness during preparation making.

Means for Solving the Problem

After intensive study to solve the above mentioned problem, the inventor of the present invention found that a preparation can be produced that stably has a rapid release property showing little pH dependency in the initial elution as well as a sufficient hardness during tablet making regardless of a tablet making method or the like (that is, even though a component of a sustained release part mixes into an immediate release part due to the tablet making method), by using a pharmaceutical form in which a medicinal ingredient is contained in both the immediate release part and the sustained release part, especially by using a specific excipient in the immediate release part and partially pregelatinized starch as an additive and making the blending proportion of each component within a specific range, in order to exert an efficacy rapidly after administration and sustain it. Thus, the inventor completed the present invention.

Therefore, the present invention relates to the following preparations.

(1) A solid pharmaceutical preparation which includes an immediate release part and a sustained release part, in which the immediate release part contains tramadol or a pharmaceutically acceptable salt thereof, partially pregelatinized starch, and an excipient.

(2) The solid pharmaceutical preparation described in (1) in which the excipient in the immediate release part includes crystal cellulose or a combination of lactose and crystal cellulose.

(3) The solid pharmaceutical preparation described in (2) in which the immediate release part contains the tramadol or the pharmaceutically acceptable salt thereof, the partially pregelatinized starch, and the crystal cellulose at 10-55% by weight, 15-45% by weight, and 8-74% by weight, respectively, per 100% by weight of the immediate release part.

(4) The solid pharmaceutical preparation described in (2) in which the immediate release part contains the tramadol or the pharmaceutically acceptable salt thereof, the partially pregelatinized starch, the lactose, and the crystal cellulose at 10-55% by weight, 15-45% by weight, 5-50% by weight, and 3-25% by weight, respectively, per 100% by weight of the immediate release part.

(5) The solid pharmaceutical preparation described in any one of (1) to (4) in which the immediate release part also includes a binding agent as an additive.

(6) The solid pharmaceutical preparation described in (5) which contains hydroxypropylcellulose as the binding agent at 0.5-3% by weight per 100% by weight of the immediate release part.

(7) The solid pharmaceutical preparation described in any one of (1) to (6) in which the tramadol or the pharmaceutically acceptable salt thereof is tramadol hydrochloride.

(8) The solid pharmaceutical preparation described in any one of (1) to (7) which is a coated tablet.

(9) The solid pharmaceutical preparation described in any one of (1) to (8) which is a bilayer tablet including the immediate release part and the sustained release part.

(10) A solid pharmaceutical preparation which includes an immediate release part and a sustained release part, in which the immediate release part contains tramadol hydrochloride, partially pregelatinized starch, and an excipient, and a dissolution rate of an active ingredient from the solid pharmaceutical preparation ranges 30-50% by weight in 15 minutes, 40-60% by weight in 1 hour, 50-70% by weight in 2 hours, 60-80% by weight in 4 hours, and 70-90% by weight in 6 hours in a dissolution test conducted according to the second test method of a dissolution test method (paddle method) of the general test method of the Japanese Pharmacopoeia using a liquid temperature of 37° C. and 900 mL of a test solution under rotation of 50 rpm.

(11) The solid pharmaceutical preparation described in (10) in which the excipient in the immediate release part is crystal cellulose or a combination of lactose and crystal cellulose.

(12) The solid pharmaceutical preparation described in (11) in which the immediate release part contains the tramadol hydrochloride, the partially pregelatinized starch, and the crystal cellulose at 10-55% by weight, 15-45% by weight, and 8-74% by weight, respectively, per 100% by weight of the immediate release part.

(13) The solid pharmaceutical preparation described in (11) in which the immediate release part contains the tramadol hydrochloride, the partially pregelatinized starch, the lactose, and the crystal cellulose at 10-55% by weight, 15-45% by weight, 5-50% by weight, and 3-25% by weight, respectively, per 100% by weight of the immediate release part.

(14) The solid pharmaceutical preparation described in any one of (10) to (13) which also includes a binding agent as an additive in the immediate release part.

(15) The solid pharmaceutical preparation described in (14) which contains hydroxypropylcellulose as the binding agent at 0.5-3% by weight per 100% by weight of the immediate release part.

(16) The solid pharmaceutical preparation described in any one of (10) to (15) which is a coated tablet.

(17) The solid pharmaceutical preparation described in any one of (10) to (16) which is a bilayer tablet including the immediate release part and the sustained release part.

Effects of the Invention

A solid pharmaceutical preparation of the present invention is a long-acting preparation that can reach an effective blood concentration rapidly after taking it and thereafter sustain its efficacy for a long period of time and that has a rapid release property showing little pH dependency in the initial elution; therefore, it is a highly useful long-acting preparation that provides a stable blood concentration of a drug independent from variation or difference in pH in digestive tract. In addition, the preparation of the present invention stably shows a rapid pH-independent behavior in the initial elution when some sustained release component are mixed into an immediate release part due to a difference of a table making method of a multilayer tablet and is a practical preparation that has a sufficient hardness enough not to occur defacement, cracking, chipping, and the like during tablet coating.

BEST MODES FOR CARRYING OUT THE INVENTION

The present invention relates to a long-acting solid pharmaceutical preparation containing tramadol as an active ingredient which has a solid pharmaceutical form including an immediate release part and an sustained release part, both of which contain an active ingredient, and in which the immediate release part contains partially pregelatinized starch and an excipient as additives. A dissolution rate of an active ingredient from the solid pharmaceutical preparation is 30-50% by weight in 15 minutes, 40-60% by weight in 1 hour, 50-70% by weight in 2 hours, 60-80% by weight in 4 hours, and 70-90% by weight in 6 hours, especially as highly rapid as 30% by weight or more in 10 minutes in initial elusion, in a dissolution test conducted according to the second test method of a dissolution test method (paddle method) of the general test method of the Japanese Pharmacopoeia using a liquid temperature of 37° C. and 900 mL of a test solution under rotation of 50 rpm. Furthermore, elution of an active ingredient continues 6 hours or later, which is beneficial for a preparation that is administered twice daily because a next administration can be done with sustained blood concentration.

A solid pharmaceutical preparation of the present invention may contain tramadol as an active ingredient or a pharmaceutically acceptable salt thereof. Tramadol is a synthetic non-narcotic analgesic agent positioned in the middle between a potent narcotic analgesic agent that is indicated for cancerous pain or the like and non-steroidal anti-inflammatory drug (NSAID) that is indicated for mild pain such as headache or arthralgia that has less frequent side effects on respiratory, circulatory, and/or digestive system compared with strong opioid such as morphine and has medical usefulness as a drug that causes resistance, physical dependence, abuse, or the like less frequently. Tramadol can be used without any limitation as long as it is a pharmaceutically acceptable acid addition salt including, for example, inorganic acid salts such as hydrochlorid, sulfate, nitrate, phosphate, hydrofluoride, and hydrobromide as well as organic acid salts such as acetate, tartrate, lactate, citrate, fumarate, maleate, succinate, methane sulfonate, benzene sulfonate, toluene sulfonate, naphthalene sulfonate, and camphor sulfonate. Especially, hydrochlorid of tramadol (tramadol hydrochloride) that is available on the market and is widely used in clinical practices as an analgesic drug is favorable. Moreover, stereoisomer, hydrate, and solvate of tramadol are also categorized as tramadol possibly to be an active ingredient of a solid pharmaceutical preparation of the present invention.

A content of tramadol in a solid pharmaceutical preparation of the present invention is not particularly limited and can be selected appropriately depending on the size of tablet and/or other factors, and, for example, a content is usually 10-70% by weight, preferably 10-65% by weight, and more preferably 10-55% by weight per 100% by weight of an immediate part of a solid pharmaceutical preparation for tramadol hydrochloride. This is because upsizing of a tablet may be needed to obtain sufficient efficacy in the case of too little content or because inconvenience in designing a preparation may occur due to a limited content of other additives in the case of too much content. The solid pharmaceutical preparation of the present invention has an immediate release part and a sustained release part, and a bilayer tablet including these two layers is a preferable embodiment, but another layer can be added appropriately. A mass ratio of a medicinal ingredient contained in each of the immediate release part and the sustained release part is not particularly limited, and tramadol hydrochloride can be favorably contained in the immediate release part and the sustained release part at a ratio of 1:1-1:5.

The solid pharmaceutical preparation of the present invention is characterized by stably having a rapid release property showing little pH dependency in the initial elution of tramadol, which is also a characteristic of composition of the immediate release part, and additives used for the immediate release part will be described below.

Partially pregelatinized starch used as an additive for the immediate release part of the solid pharmaceutical preparation of the present invention, which is dried starch grains partially pregelatinized by heating cornstarch with water under a normal or increased pressure, can be obtained using substances placed in "Japanese Pharmaceutical Excipients 2003" (edited by Japan Pharmaceutical Excipients Council and published by Yakuji Nippo Limited.) and is available as an article on the market. In the present invention, partially pregelatinized starch is appropriately contained at about 15-45% by weight, preferably 20-40% by weight, or especially preferably 20-35% by weight per 100% by weight of an immediate release part of the solid pharmaceutical preparation. Unfavorably, the used amount of around 10% allows a rate of dissolution to decrease when a component of the sustained release part is mixed into the immediate release part.

Any one or a combination among lactose, crystal cellulose, D-mannitol, calcium hydrogen phosphate, cornstarch, and potatostarch can be used as an excipient used as an additive for the immediate release part of the solid pharmaceutical preparation of the present invention, and especially crystal cellulose alone or a combination of lactose and crystal cellulose is favorable. Lactose, which is a kind of disaccharide, is used as an additive for various foods and pharmaceuticals and is available on the market, and the substance placed in the Japanese Pharmacopoeia (14th edition) can be used. In addition, crystal cellulose, which is obtained by partially depolymerizing with acid and purifying α-cellulose obtained as pulp from a fibrous plant, is available on the market, and the substance placed in the Japanese Pharmacopoeia (14th edition) can be used. In the present invention, crystal cellulose used as an excipient is appropriately contained at about 8-74% by weight, preferably 8-64% by weight, or more preferably 7-30% by weight per 100% by weight of an immediate release part of the solid pharmaceutical preparation. A combination of lactose and crystal cellulose used as an excipient is appropriately contained at about 5-50% by weight and about 3-25% by weight, preferably 5-45% by weight and 3-20% by weight, or more preferably 5-20% by weight and 2-10% by weight, respectively, per 100% by weight of the immediate release part of the solid pharmaceutical preparation.

Addition of the above components, mixing a binding agent into the immediate release part of the solid pharmaceutical preparation of the present invention is more favorable for improving physical quality. Therefore, a dosage form of the solid pharmaceutical preparation of the present invention is preferably a tablet and is required to have moderate strength as a tablet, but only partially pregelatinized starch, or an additive for providing benefit of the present invention, and an excipient may show inadequate hardness and cause defacement and/or capping (a phenomenon that a tablet is broken into a lens-like form). Therefore, addition of a binding agent enables a tablet to be prepared with more preferable hardness. Also, along with improvement in hardness, defacement, cracking, and chipping during tablet coating can be improved, which enabled the solid pharmaceutical preparation of the present invention to also be a coated tablet. To enable rapid release of the immediate release part, a preparation is required to be one with relatively limited hardness leading to rapid disintegration, though the immediate part of the solid pharmaceutical preparation of the present invention is a highly useful preparational composition that has both immediate release property and adequate hardness. As a binding agent used for the immediate release part of the solid pharmaceutical preparation of the present invention, hydroxypropylcellulose, hydroxypropylmethylcellulose, povidone, pullulan, etc. can be used, among which hydroxypropylcellulose is especially preferable. A content of hydroxypropylcellulose is not particularly limited, but a desired hardness can be obtained by using usually about 0.5-3% by weight and preferably 0.5-2% by weight per 100% by weight of the immediate release part of the solid pharmaceutical preparation.

The immediate release part of the solid pharmaceutical preparation of the present invention can contain, other than the above, various additives used for producing a general preparation as long as it will not interfere effects of the invention. Such additives include, for example, an excipient and a binding agent other than the above examples as well as a disintegrating agent, a flavoring agent, a foaming agent, a fragrance, a lubricant, and a coloring agent, which can be added appropriately depending on a purpose.

The sustained release part of the solid pharmaceutical preparation of the present invention can be prepared using a usual sustained release base, for example, a gel-forming substance or other agents that can control release of a medicinal ingredient by forming hydrogel after contacting with water. A preferable gel-forming substance includes cellulose derivatives such as hydroxypropylcellulose, methylcellulose, hydroxypropylmethylcellulose, and sodium carboxymethylcellulose, carboxyvinylpolymer, and the like, and further, a lubricant such as magnesium stearate can be added appropriately to produce the sustained release part of the solid pharmaceutical preparation of the present invention. Also, similarly to the above mentioned immediate release part, various additives used for producing a general preparation, for example, disintegrating agent, a binding agent, a flavoring agent, a foaming agent, a flavoring, a lubricant, and a coloring agent can appropriately be added to this sustained release part depending on a purpose.

The solid pharmaceutical preparation of the present invention that has the immediate release part and the sustained release part as described above can be coated if necessary. Some kinds of medicinal ingredients are preferred to being coated for the purpose of masking of bitter taste and acridity, stabilizing cardinal drug, etc., moreover coating may prevent damage and/or defacement of a tablet, which is convenient for transportation and packaging. As mentioned above, the immediate release part of the solid pharmaceutical preparation of the present invention by itself has favorable release property that have possibility to be disturbed by special coating intended to be released in a sustained manner, therefore, coating with a normal rapidly dissolving film is preferable in the present invention.

EXAMPLES

The present invention is specifically described through the following examples, but the present invention is not limited to these examples.

Example and Comparative Example

Preparation Method of a Tablet

Table 1 shows contents of respective ingredients per tablet of Examples and a Comparative Example that are prepared using a formula of a solid pharmaceutical preparation of the present invention and a formula in which an additive is different from the solid pharmaceutical preparation of the present invention, respectively (see Japanese Patent Application Publication No. JP-A-2006-96729). Respective bilayer tramadol hydrochloride tablets of the Examples (100, 75, and 50 mg of tramadol hydrochloride per tablet) and the Comparative Example (containing 100 mg of tramadol hydrochloride per tablet) having a composition as shown in Table 1 were produced according to the following preparation method.

TABLE 1

| | Formula (mg/tablet) | Example 100 mg tablet | Example 75 mg tablet | Example 50 mg tablet | Comparative Example 100 mg tablet |
|---|---|---|---|---|---|
| Immediate release part | Tramadol hydrochloride | 35.0 | 26.25 | 17.5 | 35.0 |
| | Partially pregelatinized starch | 21.0 | 17.5 | 14.0 | — |
| | Lactose | 9.0 | 17.65 | 26.2 | — |
| | Crystal cellulose | 3.9 | 7.5 | 11.2 | 4.0 |
| | Hydroxypropylcellulose | 0.7 | 0.7 | 0.7 | — |
| | Crosspovidone | — | — | — | 14.0 |
| | Erythritol | — | — | — | 12.3 |
| | Synthetic aluminum silicate | — | — | — | 4.0 |
| | Magnesium stearate | 0.4 | 0.4 | 0.4 | 0.7 |
| | Sub total | 70.0 | 70.0 | 70.0 | 70.0 |
| Sustained release part | Tramadol hydrochloride | 65.0 | 48.75 | 32.5 | 65.0 |
| | Lactose | 0.0 | 18.25 | 36.5 | 0.0 |
| | Hydroxypropylcellulose | 120.0 | 120.0 | 120.0 | 133.0 |
| | Carboxyvinyl polymer | 27.0 | 27.0 | 27.0 | 25.0 |
| | Carmellose sodium | 6.0 | 4.0 | 2.0 | 5.0 |
| | Magnesium stearate | 2.0 | 2.0 | 2.0 | 2.0 |
| | Sub total | 220.0 | 220.0 | 220.0 | 230.0 |
| | Total | 290.0 | 290.0 | 290.0 | 300.0 |

Example 1

After mixing and pulverizing 2,450 g of tramadol hydrochloride, 630 g of lactose, 273 g of crystal cellulose, and 1,470 g of partially pregelatinized starch, granulation was conducted using a solution of 49 g of hydroxypropylcellulose dissolved into purified water. To these granules, 28 g of magnesium stearate was added and mixed to be granules for an immediate release part. On the other hand, 1,625 g of tramadol hydrochloride, 3,000 g of hydroxypropylcellulose, and 150 g of carmellose sodium were mixed and pulverized to granulate using purified water. To these granules, 675 g of carboxyvinyl polymer was added and mixed followed by adding and mixing 50 g of magnesium stearate to be granules for a sustained release part. Such obtained granules for the immediate release part and the sustained release part were made into bilayer tramadol tablets that contain 100 mg of tramadol hydrochloride per tablet. Preparations that contain 75 mg or 50 mg of tramadol hydrochloride per tablet were produced in the same manner as described above except for adding and mixing lactose in addition to tramadol hydrochloride, hydroxypropylcellulose, and carmellose sodium during producing the above mentioned sustained release part.

Comparative Example

After mixing and pulverizing 350 g of tramadol hydrochloride, 123 g of erythritol, 40 g of crystal cellulose, and 40 g of synthetic aluminum silicate, granulation was conducted using purified water. To these granules, 140 g of crosspovidone was added and mixed followed by adding and mixing 7 g of magnesium stearate to be granules for an immediate release part. On the other hand, granules for a sustained release part was produced in the same manner as the above Example according to the content shown in Table 1, and obtained granules for the immediate release part and the sustained release part were made into bilayer tramadol hydrochloride tablets using a continuous tableting machine.

Test Example (1)

Dissolution Test

In each bilayer tramadol hydrochloride tablet (containing 100 mg of tramadol hydrochloride per tablet) produced in the above Example and the Comparative Example, a dissolution test was conducted according to the second test method of a dissolution test method (paddle method) of the general test method of the Japanese Pharmacopoeia (hereinafter abbreviated to as JP). The test solutions were the first solution (pH 1.2) for the disintegration test method of the general test method in JP, water, acetate-sodium acetate buffer solution (0.05 mol/L, pH4.0), and 2-fold diluted phosphate buffer solution (pH 6.8) in the Reagents and Test Solutions of JP.

After a tablet for testing was put in a 900 mL of each test solution maintained at 37° C.±0.5° C. and a dissolution test was started under rotation of 50 rpm, and then a 5 mL of eluate was sampled at every prespecified timepoint and filtered through a membrane filter with a pore size of 0.45 μm to be a sample solution. The dissolution amount of tramadol was determined in a 5 μm of sample solution using high performance liquid chromatography (HPLC). HPLC was operated using a detector (ultraviolet-absorption photometer at 271 nm), a column (ODS with dimensions of about 15 cm length× about 4 mm internal diameter), a column temperature of about 40° C., and a mobile phase (0.05% trifluoroacetic acid/acetonitrile ratio of 75:25) at a flow rate of 1.0 mL/min.

Figure 1:
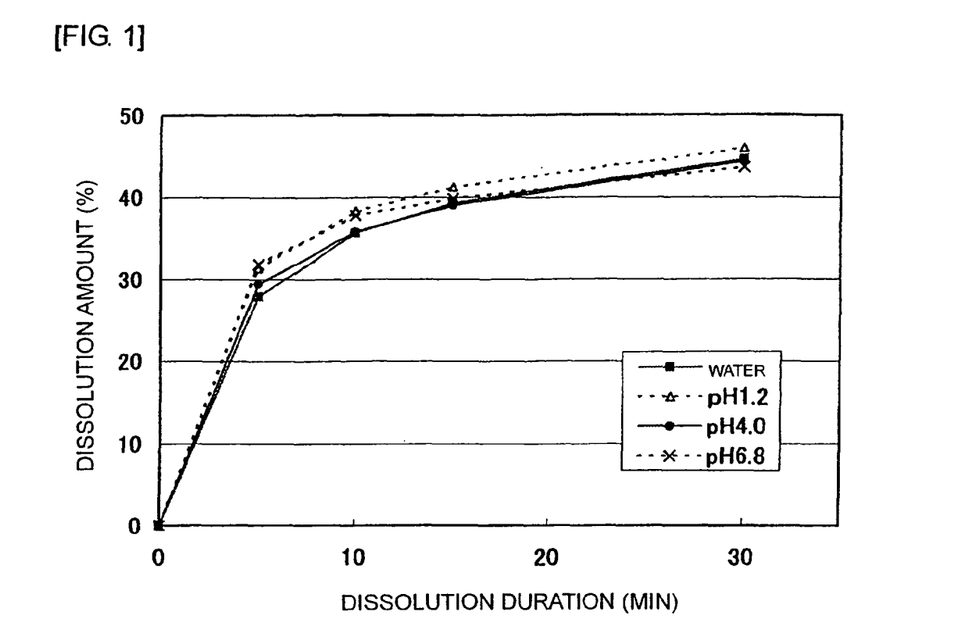
FIG. 1 is a graph showing the result of a dissolution test (for the first 30 minutes since the beginning of dissolution) of a solid pharmaceutical preparation of the present invention (containing 100 mg tramadol hydrochloride per tablet) shown in Example 1.
Figure 2:
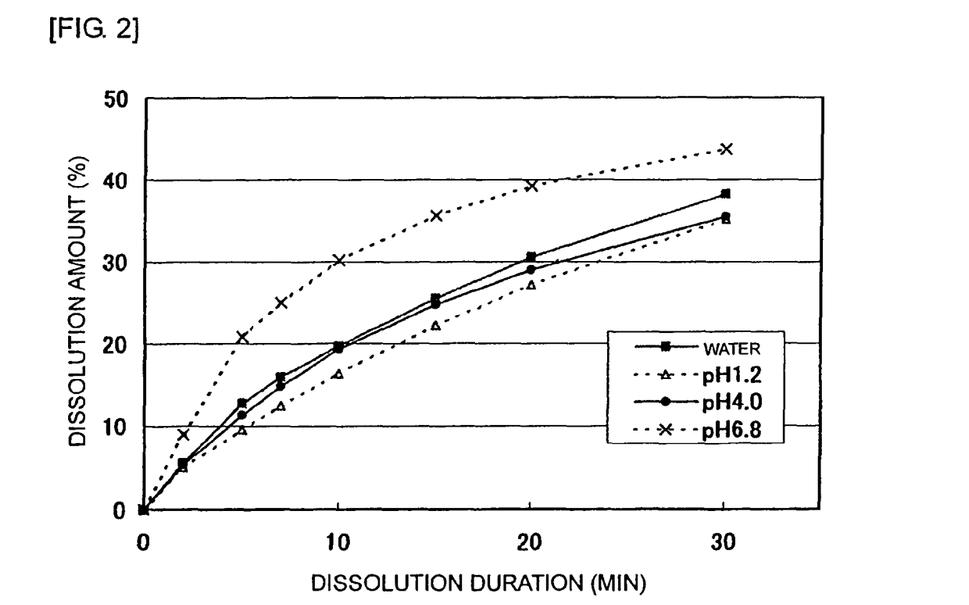
FIG. 2 is a graph showing the result of a dissolution test (for the first 30 minutes since the beginning of dissolution) of a compared solid pharmaceutical preparation (containing 100 mg tramadol hydrochloride per tablet) shown in Comparative Example.
Figure 3:
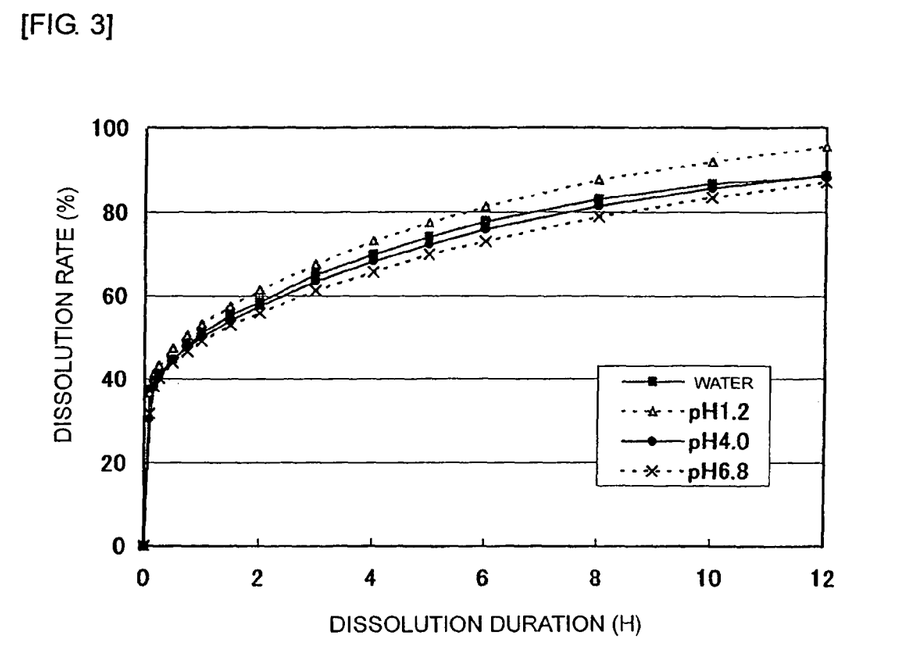
FIG. 3 is a graph showing the result of a dissolution test (for the first 12 hours since the beginning of dissolution) of the solid pharmaceutical preparation of the present invention (containing 100 mg tramadol hydrochloride per tablet) shown in Example 1.

A graph of FIG. 1 shows an example of the result at 30 minutes of dissolution in the dissolution test using a tablet produced in the Example (containing 100 mg tramadol hydrochloride per tablet), while a graph of FIG. 2 shows an example of the result at 30 minutes of dissolution in the dissolution test using a tablet produced in the Comparative Example. A graph of FIG. 3 and Table 2 show an example of the result at 12 hours of dissolution in the dissolution test using the same tablet produced in the Example.

Figure 4:
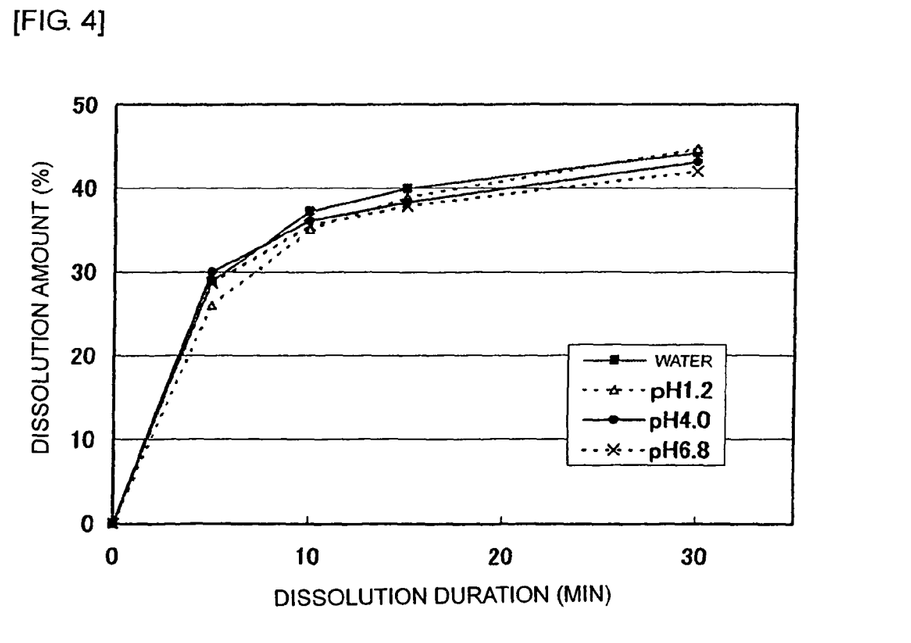
FIG. 4 is a graph showing the result of a dissolution test (for the first 30 minutes since the beginning of dissolution) of a solid pharmaceutical preparation in which 1% by weight sustained release granules was further added to an immediate release part of the solid pharmaceutical preparation of the present invention (containing 100 mg tramadol hydrochloride per tablet) shown in Example 1.
Figure 5:
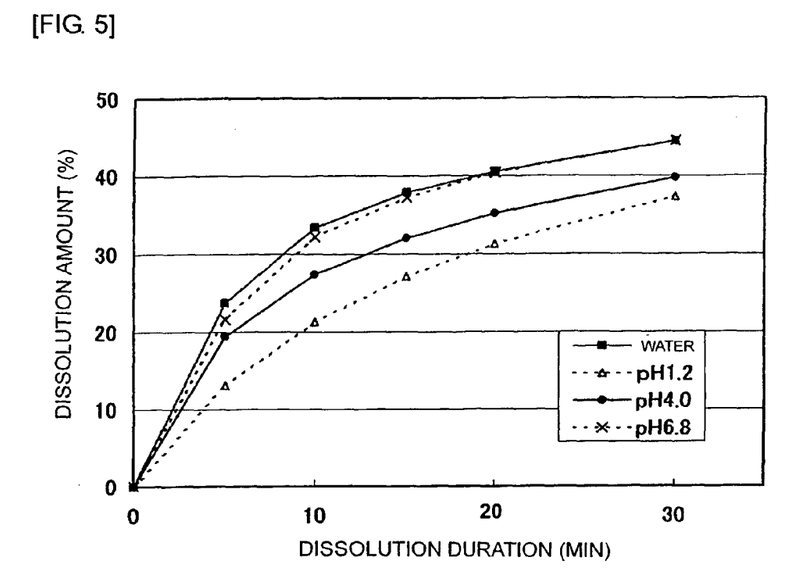
FIG. 5 is a graph showing the result of a dissolution test (for the first 30 minutes since the beginning of dissolution) of a solid pharmaceutical preparation in which 1% by weight sustained release granules was further added to the immediate release part of the solid pharmaceutical preparation of the present invention (containing 100 mg tramadol hydrochloride per tablet) shown in the Comparative Example.

On the assumption that a component of a sustained release part is mixed into an immediate release part during production using a laminating continuous tableting machine, the effect of its mixing on initial elution behavior was investigated. To be more specific, bilayer tablets were produced with granules for the immediate release part that was obtained by adding 1% by weight sustained release granules to the immediate release part of contents of the Example (containing 100 mg tramadol hydrochloride per tablet) and the Comparative Example as shown in Table 1 using a single tableting machine to conduct a dissolution test. Graphs of FIGS. 4 and 5 show an example of the result at 30 minutes of dissolution of a tablet that was obtained by adding 1% by weight sustained release granules to the immediate release part of the Example and the Comparative Example, respectively.

TABLE 2

|  |  | Dissolution rate (%) Test solutions | | | |
|---|---|---|---|---|---|
|  |  | Water | pH 1.2 | pH 4.0 | pH 6.8 |
| Dissolution duration (h) | 0 | 0.0 | 0.0 | 0.0 | 0.0 |
|  | 0.25 | 41.2 | 43.3 | 40.4 | 40.2 |
|  | 0.5 | 44.7 | 47.4 | 44.7 | 43.8 |
|  | 1 | 50.8 | 53.1 | 50.0 | 49.0 |
|  | 1.5 | 55.3 | 57.4 | 53.9 | 52.9 |
|  | 2 | 58.5 | 61.4 | 57.6 | 55.8 |
|  | 3 | 65.1 | 67.6 | 63.4 | 61.3 |
|  | 4 | 69.9 | 73.1 | 68.3 | 65.7 |
|  | 5 | 74.1 | 77.5 | 72.3 | 69.8 |

TABLE 2-continued

|  | Dissolution rate (%) Test solutions | | | |
|---|---|---|---|---|
|  | Water | pH 1.2 | pH 4.0 | pH 6.8 |
| 6 | 77.8 | 81.3 | 76.0 | 73.1 |
| 8 | 83.1 | 87.6 | 81.5 | 78.9 |
| 10 | 86.7 | 92.0 | 85.7 | 83.4 |
| 12 | 88.7 | 95.6 | 88.9 | 87.1 |

Test Example (2)

Hardness and Defacement Tests

A hardness test and a defacement test were conducted according to Tablet paragraph of General Rules for Preparations in JP in a tablet produced in the Example using the formula for the solid pharmaceutical preparation of the present invention shown in Table 1 and a tablet prepared in the same manner as the Example except for hydroxypropylcellulose from the formula. To be more specific, in the hardness test, a pressure was measured when a tablet gave in to the pressure and the tablet was destroyed. In the defacement test, about 6.5 g of tablets were precisely weighed (a) to be put in a drum of a defacement test instrument that was rotated at 25 rpm for 10 minutes, and then tablets were removed out and weighed precisely (b) to calculate a defacement rate using a following equation. Table 3 shows an example of the results of both tests.

Defacement rate (%) = $((a)-(b))/(a) \times 100$

TABLE 3

|  | Hardness (kg) | | | Defacement rate (%) | | |
|---|---|---|---|---|---|---|
|  | 100 mg tablet | 75 mg tablet | 50 mg tablet | 100 mg tablet | 75 mg tablet | 50 mg tablet |
| With no addition of hydroxypropylcellulose | 6.0 | 7.1 | 8.0 | 0.33 | 0.27 | 0.26 |
| With addition of hydroxypropylcellulose | 8.0 | 9.2 | 9.3 | 0.24 | 0.17 | 0.15 |

As demonstrated in the above tests, the solid pharmaceutical preparation of the present invention released, as shown in Table 2, about 40% by weight, about 50% by weight, about 60% by weight, about 70% by weight, and about 80% by weight tramadol hydrochloride in 15 minutes, 1 hour, 2 hours, 4 hours, and 6 hours, respectively, in respective test solutions as a result of the dissolution test conducted according to the second test method of a dissolution test method (paddle method) of the general test method of the Japanese Pharmacopoeia using a liquid temperature of 37° C. and 900 mL of a test solution under rotation of 50 rpm, indicating that the solid pharmaceutical preparation of the present invention has favorably rapid and sustained release properties. Therefore, the solid pharmaceutical preparation of the present invention is a preparation enabling tramadol hydrochloride to be released at 30-50% by weight in 15 minutes, 40-60% by weight in 1 hour, 50-70% by weight in 2 hours, 60-80% by weight in 4 hours, and 70-90% by weight in 6 hours, or preferably at 35-45% by weight in 15 minutes, 45-55% by weight in 1 hour, 55-65% by weight in 2 hours, 65-80% by weight in 4 hours, and 70-85% by weight in 6 hours, in the above dissolution test conducted using respective test solutions.

As shown in FIGS. 1 and 4, by the use of partially pregelatinized starch, crystal cellulose, lactose, or hydroxypropylcellulose as an additive in the immediate release part, the solid pharmaceutical preparation of the present invention shows excellent initial elution behavior in various types of eluates with different pH values similar to that of a tablet made using a single tableting machine, should a sustained release component be mixed into the immediate release part during production using a laminating continuous tableting machine, and releases tramadol which is an active ingredient rapidly as well as could sustain its release for a prolonged period of time. Furthermore, the preparation also has adequate hardness in terms of strength and showed no defacement, cracking, chipping, etc., during coating.

To the contrary, a preparation in the Comparative Example, which includes the immediate release part containing erythritol and crosspovidone used as primary additives, provided, as shown in FIGS. 2 and 5, the results of different patterns of initial elution behavior depending on pH value of eluates when production was performed using a continuous tableting machine. In addition, compared with the preparation produced using a single tableting machine, initial elusion was delayed significantly. This preparation of the Comparative Example showed rapid and similar initial elution behavior when it is produced using a single tableting machine even if pH of elute varies. However, such a fault as mentioned above was demonstrated when the preparation was produced using the continuous tableting machine. As a result of investigation from various aspects, this fault was considered to occur due to mixing of a sustained release component into the immediate release part caused by attaching or remaining of the sustained release part within the continuous tableting machine. However, the solid pharmaceutical preparation of the present invention showed no influence of such mixing when FIG. 4 showing initial elution behavior on the assumption that a component of the sustained release part is mixed into the immediate release part is compared with FIG. 5 showing that of the Comparative Example.

Example 2

Examination of Excipient

An immediate release part for a 100 mg tablet was prepared using Formula A in which lactose and crystal cellulose were used as an excipient and Formula B in which only crystal cellulose was used as an excipient. Table 4 shows contents of respective components per tablet. Tablets that contain 100 mg of tramadol hydrochloride per tablet and has a composition shown in Table 4 were produced according to the following preparation method.

TABLE 4

|  | Content per tablet (mg) | |
| --- | --- | --- |
| Immediate release part | Formula A | Formula B |
| Tramadol hydrochloride | 35.0 | 35.0 |
| Pregelatinized starch | 21.0 | 21.0 |
| Lactose | 9.3 | — |
| Crystal cellulose | 4.0 | 13.3 |
| Magnesium stearate | 0.7 | 0.7 |
| Total | 70.0 | 70.0 |

After mixing and pulverizing 350 g of tramadol hydrochloride, 133 g of excipient (93 g of lactose and 40 g of crystal cellulose in Formula A; 133 g of crystal cellulose in Formula B), and 210 g of partially pregelatinized starch, granulation was performed using purified water. To these granules, 7 g of magnesium stearate was added and mixed to be granules for an immediate release part.

In the same manner as Test Example (1), granules with and without 1% by weight granules for a sustained release part were prepared for Formulae A and B, respectively, and then these granules for the immediate release part and granules for the sustained release part as shown in the Table 1 were made into bilayer tramadol tablets that contains 100 mg of tramadol hydrochloride per tablet.

Test Example (3)

Dissolution Test

A dissolution test was conducted in the same manner as Test Example (1).

Figure 6:
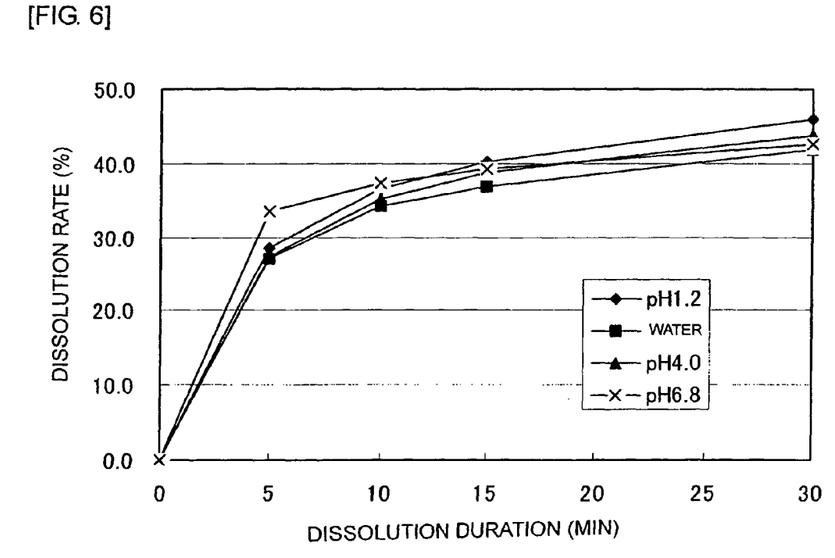
FIG. 6 is a graph showing the result of a dissolution test (for the first 30 minutes since the beginning of dissolution) of a solid pharmaceutical preparation prepared using Formula A (containing 100 mg tramadol hydrochloride per tablet) shown in Example 2.
Figure 7:
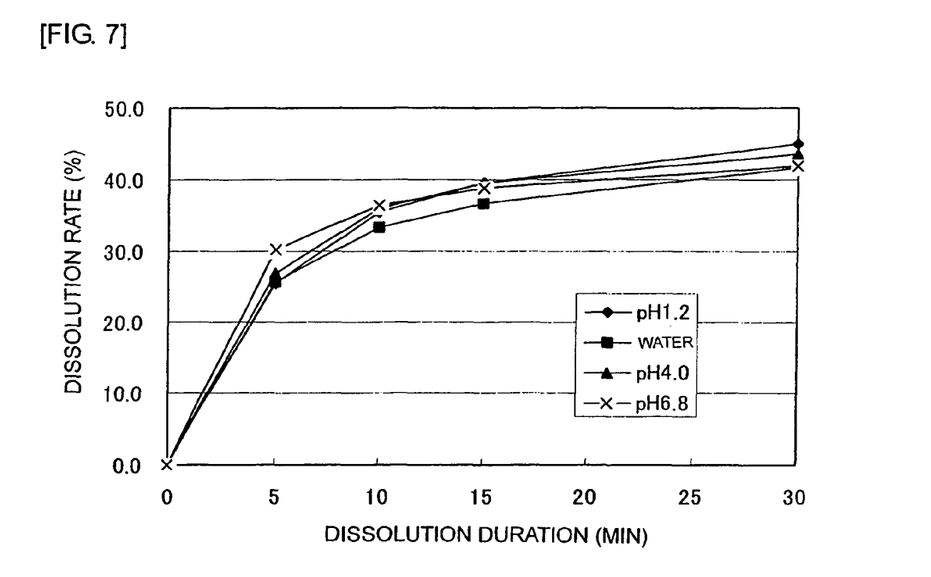
FIG. 7 is a graph showing the result of a dissolution test (for the first 30 minutes since the beginning of dissolution) of a solid pharmaceutical preparation in which 1% by weight sustained release granules was further added to the immediate release part of the solid pharmaceutical preparation prepared using Formula A (containing 100 mg tramadol hydrochloride per tablet) shown in Example 2.
Figure 8:
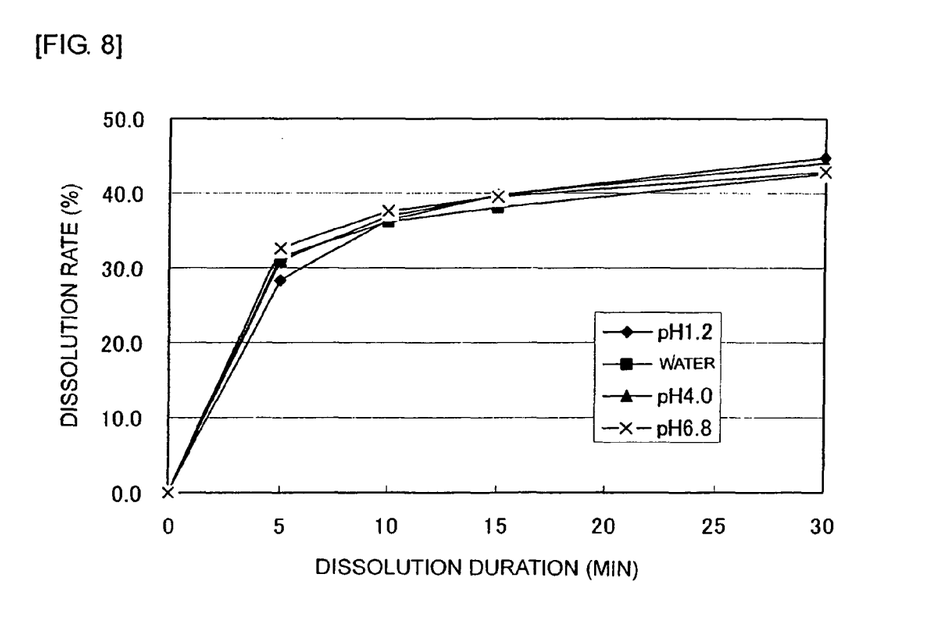
FIG. 8 is a graph showing the result of a dissolution test (for the first 30 minutes since the beginning of dissolution) of a solid pharmaceutical preparation prepared using Formula B (containing 100 mg tramadol hydrochloride per tablet) shown in Example 2.
Figure 9:
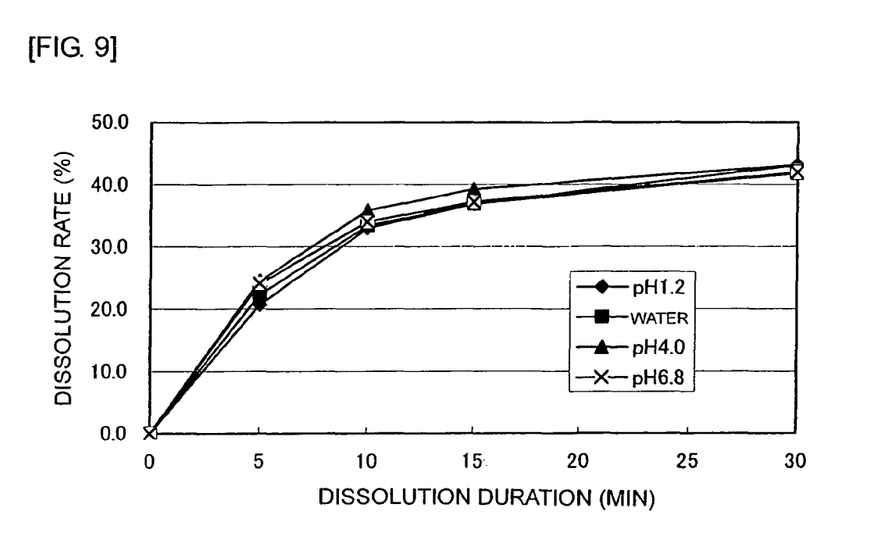
FIG. 9 is a graph showing the result of a dissolution test (for the first 30 minutes since the beginning of dissolution) of a solid pharmaceutical preparation in which 1% by weight sustained release granules was further added to the immediate release part of the solid pharmaceutical preparation prepared using Formula B (containing 100 mg tramadol hydrochloride per tablet) shown in Example 2.

A graph of FIG. 6 shows an example of the result at 30 minutes of dissolution in the dissolution test using a tablet using Formula A (containing 100 mg of tramadol hydrochloride per tablet), a graph of FIG. 7 shows an example of the result at 30 minutes of dissolution in the dissolution test using a tablet using Formula A (containing 100 mg of tramadol hydrochloride per tablet) added with 1% by weight sustained release granules, a graph of FIG. 8 shows an example of the result at 30 minutes of dissolution in the dissolution test using a tablet using Formula B (containing 100 mg of tramadol hydrochloride per tablet), and a graph of FIG. 9 shows an example of the result at 30 minutes of dissolution in the dissolution test using a tablet using Formula B (containing 100 mg of tramadol hydrochloride per tablet) added with 1% by weight sustained release granules.

Test Example (4)

Hardness and Defacement Rate Tests

Monolayer immediate release tablets (9 mmφ13R 250, 290 mg/tablet; about 10 KN) were made using Formulae A and B to conduct a hardness and a defacement rate test in the same manner as Test Example (2). The results are shown in Table 5

TABLE 5

|  | Hardness (kg) (for 100 mg tablet) | Defacement rate (%) (for 100 mg tablet) |
| --- | --- | --- |
| Formula A | 12.3 | 0.29 |
| Formula B | 14.5 | 0.15 |

As demonstrated from a comparison of FIG. 6 with FIG. 8, a tablet produced using Formula B in which only crystal cellulose was used as an excipient showed excellent pH-independent initial elution behavior similarly to a tablet produced using Formula A in which lactose and crystal cellulose were used as excipients. As realized from FIGS. 7 and 9, the inventor found it is possible that the tablet produced using Formula B in which only crystal cellulose was used as an excipient shows, similarly to the tablet produced using Formula A in which lactose and crystal cellulose were used as excipients, rapid release of tramadol as an active ingredient with excellent initial elution behavior in various types of eluates with different pH values similar to that of a tablet made using a single tableting machine should a sustained release component be mixed into an immediate release part during production using a laminating continuous tableting machine and showed its sustained release for a prolonged period of time. The tablet produced using Formula A in which lactose and crystal cellulose were used as excipients, even when 1% by weight sustained release granules was added, had a characteristic that dissolution rate at 5 minutes of early dissolution do not decrease. The tablet produced using Formula B in which only crystal cellulose was used as an excipient also had adequate hardness in terms of strength and showed no defacement, cracking, chipping, or the like of the tablet while coating.

Industrial Applicability

As described above, a bilayer solid pharmaceutical preparation containing tramadol hydrochloride that is a solid pharmaceutical preparation of the present invention is a long-acting preparation that reaches an effective blood concentration rapidly after taking for rapid pain relief and may sustain its efficacy for a long period of time and has a release property showing little pH dependency in the initial elution, and therefore is highly useful as a long-acting preparation that provides a stable blood drug concentration without influence in pH variation or difference in digestive tract. In general, such a central analgesic drug as tramadol tends to provide side effects within a lower or higher range of its blood concentration, suggesting that an efficacy range may fall in the middle of these ranges. To be more specific, to attain a blood tramadol concentration at which an effect may appear as soon as possible is considered to enable effective treatment with less side effects. The preparation of the present invention, which shows initial elution behavior as rapid as 30% by weight or more in 10 minutes in the dissolution test, enables a preferable blood tramadol concentration to be reached rapidly and enables effective treatment with less side effects. In addition, the preparation of the present invention is also a practical preparation that shows stable pH-independent and rapid initial elusion behavior should some sustained release component be mixed into an immediate release part due to a difference of a tablet making method of a multilayer tablet and has adequate hardness that prevents defacement, cracking, chipping, etc. during tablet coating.

The invention claimed is:

1. A bilayer tablet comprising:
an immediate release part; and
a sustained release part; wherein:
the bilayer tablet does not comprise a coating or is coated with a rapidly dissolving film; and
the immediate release part contains tramadol or a pharmaceutically acceptable salt thereof at 10-55% by weight, partially pregelatinized starch at 15-45% by weight, crystal cellulose at 8-74% by weight or a combination of lactose at 5-50% by weight and crystal cellulose at 3-25% by weight, and hydroxypropylcellulose as a binding agent at 0.5-3% by weight, per 100% by weight of the immediate release part.

2. The bilayer tablet according to claim 1, wherein the immediate release part contains the tramadol or the pharmaceutically acceptable salt thereof, the partially pregelatinized starch, and the crystal cellulose at 10-55% by weight, 15-45% by weight, and 8-74% by weight, respectively, per 100% by weight of the immediate release part.

3. The bilayer tablet according to claim 1, wherein the immediate release part contains the tramadol or the pharmaceutically acceptable salt thereof, the partially pregelatinized starch, the lactose, and the crystal cellulose at 10-55% by weight, 15-45% by weight, 5-50% by weight, and 3-25% by weight, respectively, per 100% by weight of the immediate release part.

4. The bilayer tablet according to claim 1, wherein the tramadol or the pharmaceutically acceptable salt thereof is tramadol hydrochloride.

5. The bilayer tablet according to claim 1, wherein the bilayer tablet is coated with the rapidly dissolving film.

6. A bilayer tablet comprising: an immediate release part; and a sustained release part; wherein: the bilayer tablet does not comprise a coating or is coated with a rapidly dissolving film; the immediate release part contains tramadol or a pharmaceutically acceptable salt thereof at 10-55% by weight, partially pregelatinized starch at 15-45% by weight, crystal cellulose at 8-74% by weight or a combination of lactose at 5-50% by weight and crystal cellulose at 3-25% by weight, and hydroxypropylcellulose as a binding agent at 0.5-3% by weight, per 100% by weight of the immediate release part; and a dissolution rate of an active ingredient from the solid pharmaceutical preparation ranges 30-50% by weight in 15 minutes, 40-60% by weight in 1 hour, 50-70% by weight in 2 hours, 60-80% by weight in 4 hours, and 70-90% by weight in 6 hours in a dissolution test conducted according to the second test method of a dissolution test method (paddle method) of the general test method of the Japanese Pharmacopoeia using a liquid temperature of 37° C. and 900 mL of a test solution under rotation of 50 rpm.

7. The bilayer tablet according to claim 6, wherein the immediate release part contains the tramadol hydrochloride, the partially pregelatinized starch, and the crystal cellulose at 10-55% by weight, 15-45% by weight, and 8-74% by weight, respectively, per 100% by weight of the immediate release part.

8. The bilayer tablet according to claim 6, wherein the immediate release part contains the tramadol hydrochloride, the partially pregelatinized starch, the lactose, and the crystal cellulose at 10-55% by weight, 15-45% by weight, 5-50% by weight, and 3-25% by weight, respectively, per 100% by weight of the immediate release part.

9. The bilayer tablet according to claim 6, wherein the bilayer tablet is coated with the rapidly dissolving film.

10. The bilayer tablet according to claim 6, wherein the dissolution rate is present at each of a pH of 1.2, 4.0, and 6.8.

* * * * *